(12) United States Patent
Myry

(10) Patent No.: US 11,291,409 B2
(45) Date of Patent: Apr. 5, 2022

(54) DEVICE FOR DETERMINING EFFECTS OF AGING OF A WEARABLE DEVICE

(71) Applicant: Clothing Plus MBU Oy, Kankaanpaa (FI)

(72) Inventor: Manu Myry, Kolkki (FI)

(73) Assignee: Clothing Plus MBU Oy, Kankaanpaa (FI)

( * ) Notice: Subject to any disclaimer, the term of this patent is extended or adjusted under 35 U.S.C. 154(b) by 994 days.

(21) Appl. No.: 14/956,458

(22) Filed: Dec. 2, 2015

(65) Prior Publication Data

US 2016/0161376 A1 Jun. 9, 2016

(30) Foreign Application Priority Data

Dec. 3, 2014 (FI) ...................................... 20146057

(51) Int. Cl.
*A61B 5/00* (2006.01)
*G16H 40/63* (2018.01)
(Continued)

(52) U.S. Cl.
CPC .............. *A61B 5/6804* (2013.01); *A61B 5/01* (2013.01); *A61B 5/024* (2013.01); *A61B 5/053* (2013.01); *A61B 5/0816* (2013.01); *A61B 5/1116* (2013.01); *A61B 5/6802* (2013.01); *G01M 99/008* (2013.01); *G16H 40/63* (2018.01); *A41D 13/1281* (2013.01); *A61B 5/0002* (2013.01); *A61B 5/0205* (2013.01); *A61B 5/02438* (2013.01); *A61B 5/1118* (2013.01); *A61B 5/6805* (2013.01); *A61B 5/7221* (2013.01);
(Continued)

(58) Field of Classification Search
None
See application file for complete search history.

(56) References Cited

U.S. PATENT DOCUMENTS 3,479,565 A 11/1969 Ross et al.
3,631,298 A 12/1971 Davis
(Continued)

FOREIGN PATENT DOCUMENTS

| CH | 662717 A5 | 10/1987 |
| CN | 200966186 Y | 10/2007 |

(Continued)

OTHER PUBLICATIONS

Merriam-Webster.com definition of loop.*
Wikipedia Entry for Impedance Matching, snapshot taken by Wayback Machine on Oct. 19, 2014 (Year: 2014).*

*Primary Examiner* — Eman A Alkafawi
*Assistant Examiner* — Leonard S Liang
(74) *Attorney, Agent, or Firm* — Young Basile Hanlon & MacFarlane, P.C.

(57) ABSTRACT

A wearable device comprises first and second transmitting loops coupled with the wearable device. The first and second transmitting loops being further coupled with a data processing unit. Additionally, the second transmitting loop may be coupled with a sensor outputting a measuring signal. The first and second transmitting loops have a property with a readable value dependent on an aging of the object of a wearable device. In addition, the data processing unit is configured to measure the value of the property of the first and second transmitting loops and determine the effects or amount of aging.

19 Claims, 3 Drawing Sheets

(51) Int. Cl.
*A61B 5/01* (2006.01)
*A61B 5/08* (2006.01)
*A61B 5/11* (2006.01)
*A61B 5/024* (2006.01)
*A61B 5/053* (2021.01)
*G01M 99/00* (2011.01)
*A41D 13/12* (2006.01)
*A61B 5/0205* (2006.01)
*A61F 13/42* (2006.01)
*G16H 40/67* (2018.01)

(52) U.S. Cl.
CPC . *A61B 2560/028* (2013.01); *A61B 2560/0223* (2013.01); *A61B 2562/029* (2013.01); *A61B 2562/0219* (2013.01); *A61B 2562/166* (2013.01); *A61F 13/42* (2013.01); *G16H 40/67* (2018.01)

(56) References Cited

U.S. PATENT DOCUMENTS

| | | | |
|---|---|---|---|
| 3,954,100 | A | 5/1976 | Sem-Jacobsen |
| 4,729,377 | A | 3/1988 | Granek et al. |
| 4,763,660 | A | 8/1988 | Kroll et al. |
| 5,450,845 | A | 9/1995 | Axelgaard |
| 5,624,736 | A | 4/1997 | DeAngelis et al. |
| 6,047,203 | A * | 4/2000 | Sackner ............ A61N 1/0452 600/388 |
| 6,080,690 | A | 6/2000 | Lebby et al. |
| 6,145,551 | A | 11/2000 | Jayaraman et al. |
| 6,210,771 | B1 | 4/2001 | Post et al. |
| 6,368,990 | B1 | 4/2002 | Jennergren et al. |
| 6,381,482 | B1 | 4/2002 | Jayaraman et al. |
| 6,400,975 | B1 | 6/2002 | McFee |
| 6,501,055 | B2 | 12/2002 | Rock et al. |
| 6,729,025 | B2 | 5/2004 | Farrell et al. |
| 6,775,566 | B2 | 8/2004 | Nissila |
| 6,941,775 | B2 | 9/2005 | Sharma |
| 7,206,630 | B1 | 4/2007 | Tarler |
| 7,559,902 | B2 | 7/2009 | Ting et al. |
| 7,637,747 | B2 | 12/2009 | Jaatinen et al. |
| 7,712,373 | B2 | 5/2010 | Nagle et al. |
| 8,003,887 | B1 | 8/2011 | Hsieh et al. |
| 8,224,418 | B2 | 7/2012 | Birnbaum et al. |
| 8,704,758 | B1 | 4/2014 | Figley et al. |
| 8,750,959 | B2 | 6/2014 | Lindberg et al. |
| 8,945,328 | B2 * | 2/2015 | Longinotti-Buitoni ............ A61B 5/0002 156/234 |
| 8,948,839 | B1 * | 2/2015 | Longinotti-Buitoni ............ A61B 5/6804 29/825 |
| 9,282,893 | B2 * | 3/2016 | Longinotti-Buitoni ............ A61B 5/6804 |
| 9,498,128 | B2 * | 11/2016 | Jayalath ............ A61B 5/0022 |
| 9,817,440 | B2 * | 11/2017 | Longinotti-Buitoni ............ A61B 5/6804 |
| 9,848,826 | B2 * | 12/2017 | Volpe ............ A61B 5/0205 |
| 10,037,672 | B1 * | 7/2018 | Abraham ............ G08B 21/0453 |
| 10,045,439 | B2 * | 8/2018 | Longinotti-Buitoni ............ A61B 5/6804 |
| 10,258,092 | B2 * | 4/2019 | Longinotti-Buitoni ............ A61B 5/0002 |
| 10,462,898 | B2 * | 10/2019 | Longinotti-Buitoni ............ D06M 11/74 |
| 2002/0026112 | A1 | 2/2002 | Nissila et al. |
| 2002/0076948 | A1 * | 6/2002 | Farrell ............ B32B 3/08 438/800 |
| 2002/0082491 | A1 | 6/2002 | Nissila |
| 2002/0124295 | A1 | 9/2002 | Fenwick et al. |
| 2002/0154518 | A1 * | 10/2002 | Elferich ............ H02J 7/025 363/15 |
| 2003/0223263 | A1 * | 12/2003 | Jacob ............ H01L 27/108 365/145 |
| 2003/0224685 | A1 | 12/2003 | Sharma |
| 2005/0054941 | A1 | 3/2005 | Ting et al. |
| 2005/0275416 | A1 | 12/2005 | Hervieux et al. |
| 2006/0124193 | A1 | 6/2006 | Orr et al. |
| 2006/0152377 | A1 | 7/2006 | Beebe et al. |
| 2006/0224072 | A1 | 10/2006 | Shennib |
| 2006/0267790 | A1 | 11/2006 | Matthiessen et al. |
| 2007/0073131 | A1 | 3/2007 | Ryu et al. |
| 2007/0083096 | A1 | 4/2007 | Paradiso |
| 2007/0100666 | A1 * | 5/2007 | Stivoric ............ A61B 5/0008 705/3 |
| 2007/0177298 | A1 | 8/2007 | Jaatinen et al. |
| 2007/0285868 | A1 | 12/2007 | Lindberg et al. |
| 2007/0298666 | A1 | 12/2007 | Kurth |
| 2008/0039687 | A1 * | 2/2008 | Shimizu ............ A61B 1/00036 600/117 |
| 2008/0064964 | A1 * | 3/2008 | Nagata ............ A61B 5/0205 600/484 |
| 2008/0208029 | A1 | 8/2008 | Thijs et al. |
| 2008/0287770 | A1 | 11/2008 | Kurzweil et al. |
| 2009/0012408 | A1 * | 1/2009 | Nagata ............ A61B 5/282 600/484 |
| 2009/0018428 | A1 | 1/2009 | Dias et al. |
| 2009/0112079 | A1 | 4/2009 | Hassonjee et al. |
| 2009/0173529 | A1 | 7/2009 | Lee et al. |
| 2009/0281394 | A1 | 11/2009 | Russell et al. |
| 2009/0287426 | A1 * | 11/2009 | Kukowski ............ G01R 31/58 702/35 |
| 2010/0198043 | A1 * | 8/2010 | Holzer ............ A41D 13/1281 600/388 |
| 2010/0298899 | A1 | 11/2010 | Donnelly et al. |
| 2011/0160601 | A1 | 6/2011 | Wang et al. |
| 2011/0213208 | A1 | 9/2011 | McKenna et al. |
| 2011/0282164 | A1 | 11/2011 | Yang et al. |
| 2013/0085538 | A1 | 4/2013 | Volpe et al. |
| 2013/0160183 | A1 | 6/2013 | Reho et al. |
| 2013/0274587 | A1 | 10/2013 | Coza et al. |
| 2013/0281795 | A1 | 10/2013 | Varadan |
| 2013/0321168 | A1 | 12/2013 | Mahony et al. |
| 2014/0015410 | A1 | 1/2014 | Shibata et al. |
| 2014/0070957 | A1 * | 3/2014 | Longinotti-Buitoni ............ G06F 3/011 340/870.01 |
| 2014/0090146 | A1 | 4/2014 | Yeomans et al. |
| 2014/0275883 | A1 | 9/2014 | Haisley et al. |
| 2014/0318699 | A1 * | 10/2014 | Longinotti-Buitoni ............ A61B 5/0002 156/247 |
| 2014/0343392 | A1 | 11/2014 | Yang |
| 2015/0025354 | A1 | 1/2015 | Salonius et al. |
| 2016/0038083 | A1 * | 2/2016 | Ding ............ A61B 5/6804 600/388 |
| 2016/0249698 | A1 * | 9/2016 | Berzowska ........ A41D 13/0015 2/69 |
| 2017/0082418 | A1 * | 3/2017 | Gong ............ A61B 5/1072 |
| 2018/0010902 | A1 * | 1/2018 | Gong ............ A61B 5/1072 |
| 2018/0317814 | A1 * | 11/2018 | Nurkka ............ A61B 5/6805 |

FOREIGN PATENT DOCUMENTS

| | | |
|---|---|---|
| CN | 201114998 Y | 9/2008 |
| DE | 10338029 A1 | 4/2005 |
| DE | 102004058731 A1 | 6/2006 |
| EP | 0509689 A2 | 10/1992 |
| EP | 0855167 A1 | 7/1998 |
| EP | 0947967 A1 | 10/1999 |
| EP | 1095612 A1 | 5/2001 |
| EP | 1504739 A1 | 2/2005 |
| EP | 1632926 A1 | 3/2006 |
| EP | 1676528 A1 | 7/2006 |
| EP | 1894523 A1 | 3/2008 |
| EP | 2057943 A1 | 5/2009 |
| EP | 2082967 A1 | 7/2009 |
| EP | 2975915 A1 | 1/2016 |
| FI | 119456 B | 11/2008 |
| FI | 119716 B | 2/2009 |
| GB | 2257523 A | 1/1993 |
| GB | 2503716 A | 1/2014 |

(56) References Cited

FOREIGN PATENT DOCUMENTS

| | | |
|---|---|---|
| WO | 99/64657 A2 | 12/1999 |
| WO | 00/19957 A1 | 4/2000 |
| WO | 00/44411 A1 | 8/2000 |
| WO | 01/01855 A1 | 1/2001 |
| WO | 01/02052 A2 | 1/2001 |
| WO | 01/48291 A1 | 7/2001 |
| WO | 01/49912 A1 | 7/2001 |
| WO | 01/78577 A2 | 10/2001 |
| WO | 02/30279 A1 | 4/2002 |
| WO | 02032665 A1 | 4/2002 |
| WO | 02/40091 A2 | 5/2002 |
| WO | 02/071935 A1 | 9/2002 |
| WO | 02/098659 A1 | 12/2002 |
| WO | 03/010561 A2 | 2/2003 |
| WO | 2006/029105 A2 | 3/2006 |
| WO | 2006/068811 A1 | 6/2006 |
| WO | 2006/094152 A2 | 9/2006 |
| WO | 2006/128957 A1 | 12/2006 |
| WO | 2006/129272 A2 | 12/2006 |
| WO | 2007/050650 A2 | 5/2007 |
| WO | 2007/107906 A1 | 9/2007 |
| WO | 2008/071843 A1 | 6/2008 |
| WO | 2009/107906 A1 | 9/2009 |
| WO | 2012/176193 A1 | 12/2012 |
| WO | 2013033238 A1 | 3/2013 |
| WO | 2015/136521 A1 | 9/2015 |

\* cited by examiner

DEVICE FOR DETERMINING EFFECTS OF AGING OF A WEARABLE DEVICE

CROSS REFERENCE TO RELATED APPLICATION

This application claims the benefit of Finnish Patent Application No 20146057 filed on Dec. 3, 2014, which is incorporated by reference as if fully set forth.

FIELD OF INVENTION

The invention relates to a device for determining effects of aging of a wearable device or an object integrated into the wearable device, such as a garment. Especially the invention relates to determining effects of aging related to a wearable sensor, object or device. In addition the invention relates to a method of manufacturing the devices.

BACKGROUND

In general, devices and especially wearable devices wear or age during use. In some cases there is a need for determining a level of aging of the device, such as especially wearable devices, like apparels, garments or clothing, and in particularly sport or activity apparels. In addition it is commonly known that the wearable devices may nowadays comprise plurality of electronic sensors, including e.g. sensors and data processing units, as well as electrical wires or other data communication lines integrated into the wearable devices, especially into the apparels, garments or clothing, for transmitting e.g. measured electrical signals between the sensors, sensors or data processing units or the like.

There are however some disadvantages relating to the known prior art, such as e.g. when the wearable device ages, the aging affects to electrical or other properties of the sensors, sensors and especially to the electrical wires or other data communication lines changes. For example resistance of the electric wire connecting the data processing units and the measuring sensor may change due to aging or e.g. mechanical stress, whereupon it causes error or deviations to the signal, e.g. measured resistance, detected by the data processing units.

SUMMARY

In view of the above, it is thus an object of the invention is to alleviate and eliminate the problems relating to the known prior art. An object of the invention is to provide a device for determining effects of aging of an object of a wearable device, such as aging of a signal transmitting lines or wires or the like, aging of the wearable device itself or aging of a portion of the wearable device. The aging should be understood as a time based aging or aging due to mechanical or stress based aging or deterioration, detrition, erosion or abrasion or all of these. An additional object of the invention is to compensate the measured signals by taking into account the effects of the aging.

According to an embodiment of the invention a wearable device comprises an object integrated into the wearable device as well as an arrangement for determining effects of aging of an object of a wearable device. The object may be e.g. the wearable device, like garment itself, or any electrical wiring or conductor, such as printed conductor in or on the wearable device, as an example. The arrangement comprises first and second transmitting loops coupled with the wearable device and connected to a data processing unit. The second transmitting loop may also be coupled with an end device, such as a sensor outputting a measuring signal. In addition the loops have a property with a readable value, where the readable value depends on an aging of the object of a wearable device, whereupon the data processing unit measures the value of the property of the first and second transmitting loop and thereby determines effects or amount of the aging, as is described in more details elsewhere in this document.

According to an embodiment the first and second transmitting loops are physically the same one transmitting loop, whereupon the measurements of the value of the property are made sequentially, so the first measurement is done at the first moment and the second measurement is done at the second moment being later than said first moment (the loops are thus construed to be physically one loop and functionally in time as two loops). In this embodiment the effects of the aging are determined by comparing the sequentially measured results with each other and thereby determining the aging via the changed measured values.

Alternatively or in addition to a baseline or factory value of said property of said loop can be used for determination of aging. In this case it is advantageous to know the baseline or factory value (property) of the loop at a first time, whereupon the read current value can be compared to the baseline or factory value. When the trend or dependency or behavior of the property of the loop is known in function of time, the effects or amount of aging can be determined based on the comparison of the current value to the baseline or factory value. For example it is known that baseline or factory value for resistance of a certain loop is $\Omega 1$ at first, but during time i.e. due to aging the resistance of said loop for example increases linearly (or other manner), whereupon the degree of the aging can be estimated and determined based on current reading and comparing to known behavior or trend of that component property. In practice the data processing unit may be configured to determine the effects or amount of aging by comparing the currently read value of said property at a second time to said baseline or factory value.

As an example, resistance of a printed conductor will increase in time, whereupon the aging can be determined via determining changes in resistance in time. Thus according to an example at least portion of the first and/or second transmitting loops is advantageously printed conductive conductor.

Also other electrical properties of the loop can be detected, such as conductance, capacitance or inductance. In addition the property may also be another property, such as an optical property, like intensity, polarization or wavelength. When the behavior or changes of the property in time or under mechanical pressure or under loading is known, the effect or amount of aging can be determined. Therefore the loops may be e.g. electrically or optically implemented loops, whereupon they are coupled with the data processing unit advantageously either galvanically and/or optically, and the property is electrical or optical property.

According to another embodiment the first and second transmitting loops are physically separate transmitting loops, whereupon the measurements of the value of the property can be made simultaneously and the aging is determined via comparing the results of the first and second values with each other.

In addition, according to an embodiment, the first and second transmitting loops are separate transmitting loops and the property with a readable value depending on aging of the object of a wearable device is a mutual property of at least two physically separate loops, such as capacitance or resistance between two adjacent loops. This is for example the case where the loops are arranged into the wearable device next to each other, whereupon the mutual property, such as capacitance or conductance (resistance) between the first and second loops have a certain value at the beginning (so at the first moment of time t1). Then, when the wearable device is getting older (ages), it typically absorbs sweat and salts, whereupon the value of the mutual property will change. In this case the aging can be determined based on the changing value of the mutual property so for example when the value of capacitance or conductance (resistance) has changed over a certain limit or threshold value, the effect or amount of aging can be deduced.

According to an embodiment, separate first and second transmitting loops may also comprise different material selected advantageously so that the first material has a property, which depends on aging essentially differently than said second material. For example erosion of the first material may be much higher during time and usage of the wearable device that its resistance or other property changes much more that the one of said second material. Examples of materials are e.g. carbon ink, silver ink or copper. Based on this different rate of changing the aging can be deduced. For example resistance of a printed ink conductor will change more rapidly than e.g. resistance of a copper wire integrated into the wearable device. Very analogously the first transmitting loop may comprise first physical structure, which differs essentially from a physical structure of the second transmitting loop. The structures are advantageously selected so that the first physical structure depends on aging essentially differently than the second physical structure. The first structure may be for example a thick printed conductor and the second structure a thin printed conductor, whereupon their resistances will change essentially differently during usage or time. For example the resistance or other property of the first structure changes much more that the one of said second material during usage or time. In addition the location of the separate transmitting loops can be selected in said wearable device so that the first transmitting loop will be exposed to higher erosion than the second transmitting loop during usage, whereupon the aging can again be detected by comparing the different rates of changing of the properties, such as different rates of changing of resistances of the loops.

The determined effect or amount of the aging can be used to provide notification of either aging level of the object or notification, such as an indication via a LED light or sound device that the object or the wearable device is over aged based on said determined effect or amount of aging. According to an embodiment, the data processing unit may send information related to the determined effect or amount of the aging further e.g. to an outer device, such as a smart phone or the like, which then can provide notification or even further process said data and provide an indication about the aging level of the object or that the object or the wearable device is over aged. Alternative, or in addition, the determined effect or amount of the aging (or even the measured difference in the values of the property) can be used to manipulate, such as compensate or correct, the measured signals read via the second transmitting loop. The signal manipulation may be based on the value of the property of the first transmitting loop.

According to an embodiment, the second transmitting loop may be a loop or conductor, such as a printed conductor, used for powering an end device, like a LED light source, heating element, antenna, intelligent component or the like, whereupon the determined effect or amount of the aging of the first transmitting loop can be used to manipulate the fed power to the second transmitting loop and again to the end device, such as adjusting the electric current or voltage and thereby compensating possible changes in conductivity of the second transmitting loop.

The wearable device may be a garment or a structure portion of the garment, such as a strap or belt, heart rate sensor strap, shirt, belt, sleeve, back or front portion of a shirt, leg, pocket, brand label, elastic portion of the garment, hat, bra, underwear, jacket, trousers, swimming suit, band, shoe, sock and/or glove, for example. The sensor may be a sensor for detecting biosignals, heart rate, respiration rate, posture of the user, temperature, humidity, conductivity, and/or acceleration, for example.

The present invention offers advantages over the known prior art, such as the possibility to determine the degree of the aging of the object, such as aging of the printed loops integrated into the garment or even the garment as such. In addition according to the invention the effects or amount of the aging can be taken into account in order to correct e.g. measuring signals, because the aging causes changes into the property of the measuring lines, such as to the printed conductors, which is especially important when measuring very weak signals or where the sensor as such determines e.g. changes in resistance, whereupon the resistance changes in the measuring loop due to aging are highly important.

The object of the invention can be achieved by the features of the claims. The invention relates to a wearable device according to claim 1. In addition the invention relates to a manufacturing method of a wearable device according to claim 17.

It is further noted that the invention relates to all possible combinations of features unless explicitly stated otherwise.

BRIEF DESCRIPTION OF THE DRAWINGS

The above, as well as additional objects, features and advantages of the present invention, will be better understood through the following illustrative and non-limiting detailed description of preferred embodiments of the present invention, with reference to the appended drawings, where the same reference numerals will be used for similar elements, wherein:

FIG. 1 illustrates principles of exemplary prior art devices for measuring signals;

FIG. 2 illustrates principles of exemplary prior art devices for measuring signals;

FIG. 3 illustrates exemplary loop constructions for determining effect or amount of aging according to an embodiment of the invention;

FIG. 4 illustrates exemplary loop constructions for determining effect or amount of aging according to an embodiment of the invention;

FIG. 5 illustrates exemplary loop constructions for determining effect or amount of aging according to an embodiment of the invention;

FIG. 6 illustrates exemplary loop constructions for determining effect or amount of aging according to an embodiment of the invention;

DETAILED DESCRIPTION OF THE PREFERRED EMBODIMENTS

Figure 7:
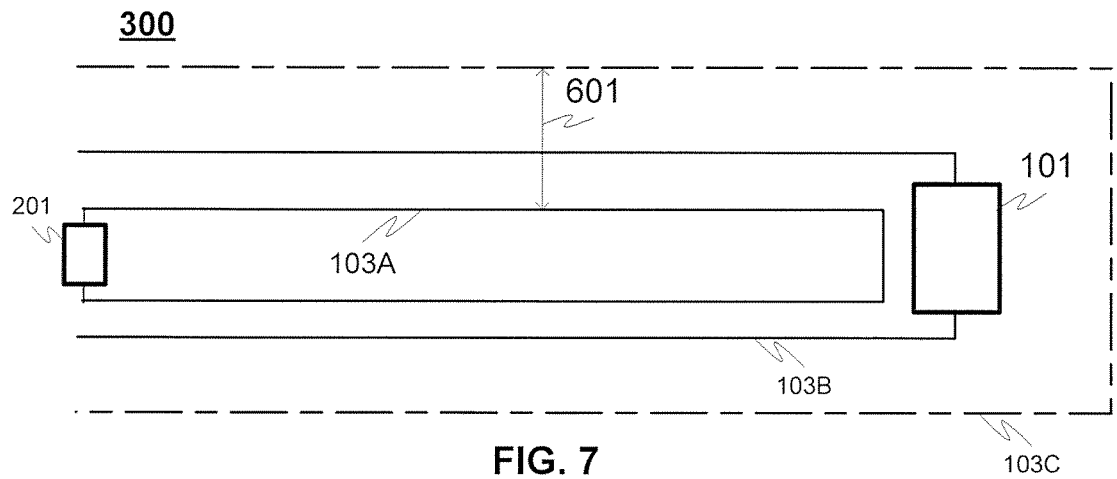
FIG. 7 illustrates exemplary loop constructions for determining effect or amount of aging according to an embodiment of the invention.

The present invention will now be described more fully hereinafter with reference to the accompanying drawings, in which embodiments of the invention are shown. The systems and devices disclosed herein will be described during operation.

Figures 1, 2, 3, 4, 5, 6:
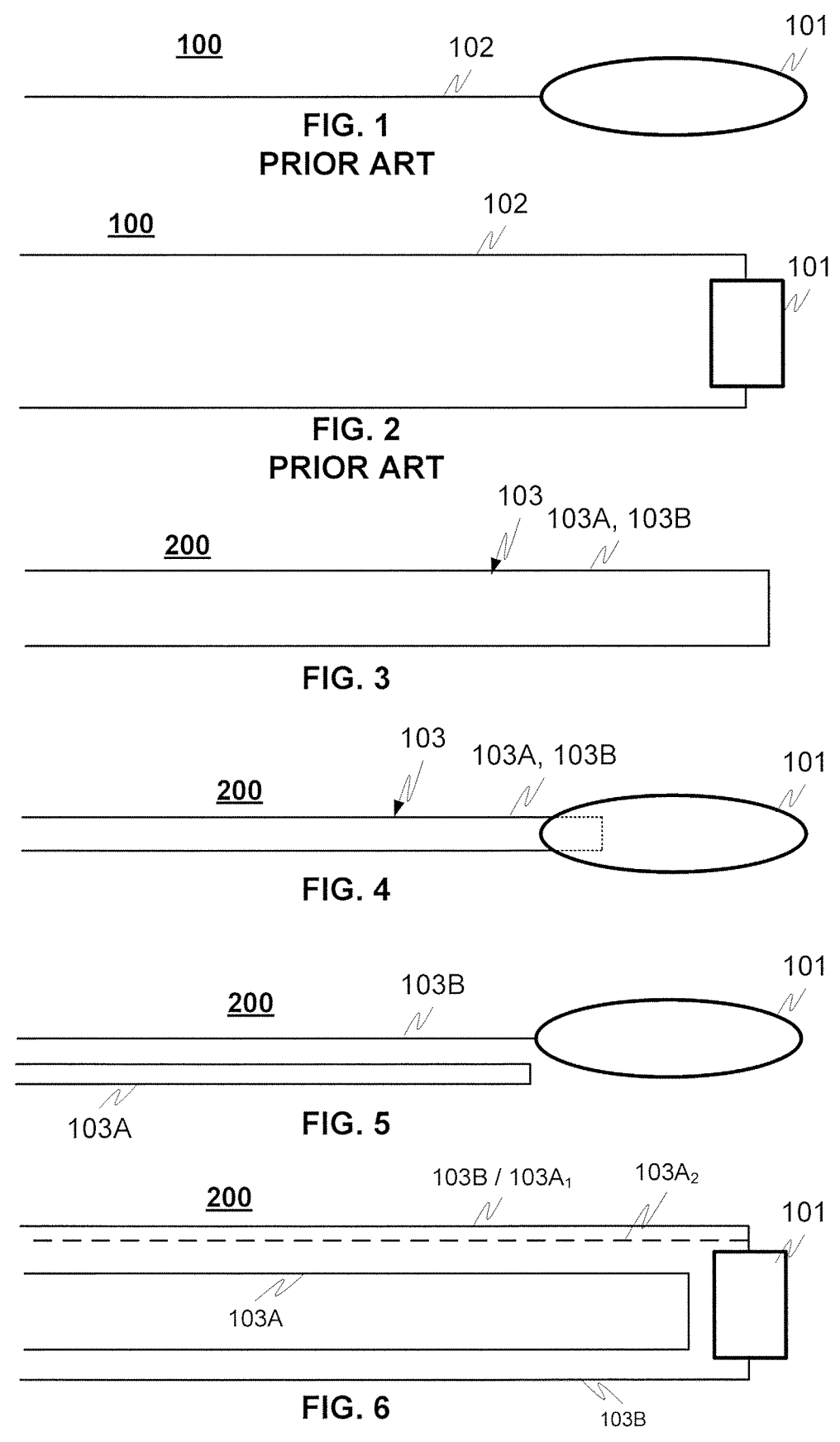

FIGS. 1-2 illustrate principles of exemplary prior art arrangements 100 for measuring signals. These arrangements 100 may be integrated into the garment for measuring biosignals via a sensor 101, such as voltage induced by heart rate (FIG. 1) or e.g. body temperature via thermocouple illustrated in FIG. 2. The conductors 102 may be implemented e.g. by a copper conductors, which are however uncomfortable. Nowadays printed conductors are used because they are comfortable and are very durable. However the problems related to the printed conductors include e.g. the changes in resistances in time and due to mechanical stress and loads. The changes in resistances in the conductors 102 easily causes interferences to the measuring signals, especially when the measuring signals are weak or base on measuring resistance or other property, to which the aging also affects in the conductors 102.

FIG. 3-7 illustrate exemplary loop constructions for determining effect or amount of aging according to an advantageous embodiment of the invention. In FIG. 3 the loop construction or the arrangement 200 comprises actually one physical transmitting loop 103, which is however construed to function functionally as said first and second transmitting loops so that the transmitting loop 103 functions as the first transmitting loop 103A at the first moment and as the second transmitting loop 103B at the second moment being later than said first moment. In this embodiment, the effects or amount of aging are determined by comparing the sequentially measured results with each other and thereby determining the aging via the changed measured values. Thus the measurement of aging is not continuous, but must be made sequentially. For example change of resistance or other value of the loop is dependent on time, whereupon the aging can be determined based on the change of resistance or other value.

In FIG. 4 the loop construction or the arrangement 200 comprises the transmitting loop 103, which corresponds with the case described in FIG. 3, but the transmitting loop is additionally coupled with a sensor 101. The arrangement 200 in FIG. 4 is construed to function as said first and second transmitting loops 103A, 103B so that the transmitting loop 103 functions as the first transmitting loop 103A at the first moment (reference loop) and as the second transmitting loop 103B (measuring loop) at the second moment measuring the reading of the sensor 101. In this embodiment, the effect of aging is taken into account by comparing sequentially measured results of the transmitting loop 103A, when functioning as said reference loop and not as said measuring loop. Thus the measurement of aging is not continuous. Thereby the effects or amount of aging can also be taking into account in the measured signal of the sensor.

In FIG. 5 the arrangement comprises the second transmitting loop 103B coupled with the sensors 101, as well the first transmitting loop 103A coupled advantageously with the wearable device and functioning as a reference loop. The term loop is used even if the measurement can be done by one wire. There the signal measurement by the second transmitting loop 103B and the aging determination via the first transmitting loop 103A can be done simultaneously. Also the effect or amount of aging can be taken into account at every turn when measuring either signal.

FIG. 6 illustrates an arrangement 200, where the second transmitting loop 103B is again coupled with the sensor 101. The first transmitting loop 103A functioning as a reference loop may be either a separate loop of the second transmitting loop 103B and thus corresponding the embodiment of FIG. 5. Alternatively one branch 103A1 of the first transmitting loop 103B can be implemented by the first branch 103A1 of the second transmitting loop 103B and the second branch (as a return channel) 103A2 of the first transmitting loop can be implemented by a separate branch (dashed line), whereupon the signal measurement by the second transmitting loop 103B and the aging determination via the first transmitting loop 103A, 103A1, 103A2 can be done simultaneously, as was the case also in FIG. 5.

FIG. 7 illustrates an arrangement 300, where the first 103A and second (or third) 103C transmitting loops are separate transmitting loops. In addition the arrangement may additionally comprise an end device or sensor 101 for detecting biosignals, which has own loop for transferring measuring signal. According to an example the property to be measured and depending on the aging of the object of a wearable device is a mutual property 601 of said loops 103A 103B, such as electrical property, like capacitance or resistance between said loops. When the object of the wearable device (and thus the device itself) ages, the mutual property 601, such as capacitance or resistance between said loops, changes. Typically the wearable device and object absorbs sweat including e.g. salts, which will be trapped into the porosity material structure of the wearable device and object and thus changes electrical properties between said loops, such as capacitance or resistance. When the mutual property 601 (e.g. electrical property) is changed over a predetermined threshold value, it can be construed that the object of the wearable device is then aged and should be e.g. disposed of or changed. The mutual property 601 may be understood also according to an embodiment as a short circuit in an electrical way at the situation where the object of the wearable device is aged.

According to an example, the first 103A and second 103C transmitting loops are selected so that their properties (readable values or measurable properties) depend on aging in different ways. For example, the electrical property of the first loop 103A material (e.g. carbon ink) changes more rapidly during aging than the electrical property of the second loop material (e.g. silver ink), whereupon the trend or amount of difference between these two values implies the aging of the object of the wearable device. Also or alternatively, the physical structure of the first and second loops 103A, 103C may differ which each other and selected so that e.g. electrical property of the structure (e.g. thin, zigzag printed loop) of the first loop 103A changes more rapidly during aging than the electrical property of the second loop structure (e.g. thick and wide straight printed loop), whereupon the trend or amount of difference between these two values implies the aging of the object of the wearable device.

In addition it is to be noted that the arrangement may also comprise a reference component, such as a resistance 201 corresponding to the original resistance (or other property) of the sensor 101, whereupon the compensation for the measured signal of 101 can be compensated by using the value of the component 201, to which said aging does not influence as it does to the component or sensor 101.

Figure 8:
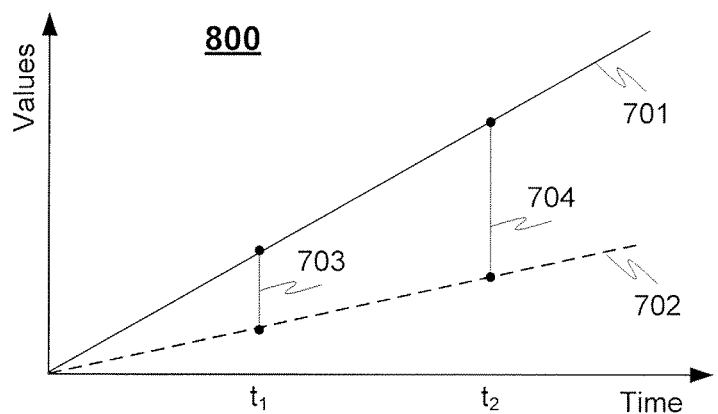
FIG. 8 illustrates exemplary diagram of changing properties of two different loops in function of time according to an embodiment of the invention.

FIG. 8 illustrates exemplary diagram 800 of changing properties of two different loops 103A, 103B, 103C in function of time according to an advantageous embodiment of the invention, where the property 701 of the first loop changes more rapidly during aging than the property 702 of the second loop. For example, at the first time moment t1 the difference of the properties between the first and second loops has a certain first value 703, whereas at the second moment t2 later than said first moment the difference has a certain second value 704 being greater than said first value at the first moment. Therefore the trend or amount of differences 703, 704 between these two values implies the aging of the object of the wearable device.

Figure 9:
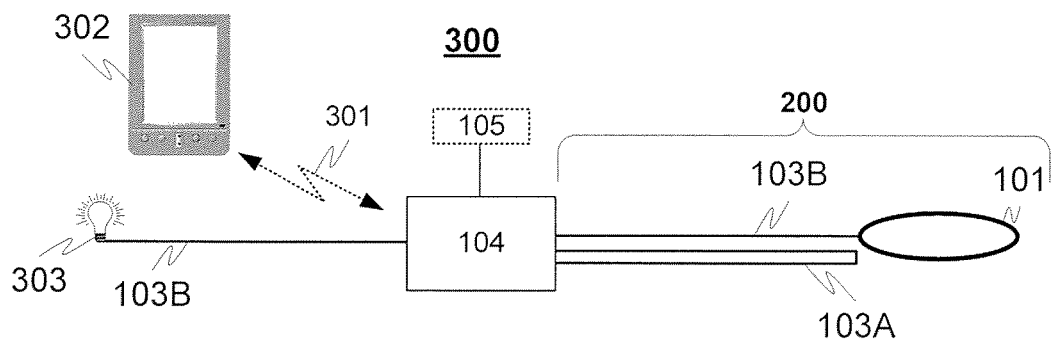
FIG. 9 illustrates exemplary arrangement for determining effect or amount of aging according to an embodiment of the invention.

FIG. 9 illustrates an exemplary arrangement 300 for determining effect or amount of aging according to an advantageous embodiment of the invention, where the arrangement 300 comprises any of previous arrangement illustrated in FIGS. 3-7 with the first and second transmitting loops. The arrangement 300 advantageously comprises a data processing unit 104, wherein the first and second transmitting loops are coupled with said data processing unit. The coupling may be made galvanically and/or optically, depending on the type of the loop and the property to be read (electrical or optical property).

The data processing unit may be any known data processing unit, which is configured to measure the value of said property of the first and second transmitting loops 103A, 103B and thereby determine effects or amount of aging, as depicted elsewhere in this document. In addition according to an embodiment the data processing unit is advantageously configured to provide indication for example via an indication device 105 of either aging level of the object, where it is integrated, or notification (such as LED light or sound or the like 105) that the object or the wearable device is over aged based on said determined effect or amount of aging. Alternatively, or in addition to, the data processing unit 104 may be configured to communicate 301 the determined effect or amount of the aging further e.g. to an outer device 302, such as a smart phone or the like, which then can provide notification or even further process said data and provide an indication about the aging level of the object or that the object or the wearable device is over aged.

Again it is to be noted that the arrangement 200, 300 may comprise plurality of first transmitting loops 103A and/or second transmitting loops 103B. In addition the arrangement 200, 300 may comprise also an end device 303, such as a LED light source, whereupon at least one second transmitting loop 103B (left in FIG. 9) may be used for powering it.

Furthermore according to an embodiment the data processing unit 104 is advantageously configured to manipulate, such as compensate or correct, the measured signals read via the second transmitting loop 103B based on the value of the property of the first transmitting loop, when this is possible so when the signal reading from the sensor is read (e.g. arrangements in FIGS. 5, 6), or to manipulate the fed power to the second transmitting loop 103B (left in FIG. 9) and again to the end device 303.

Figure 10A:
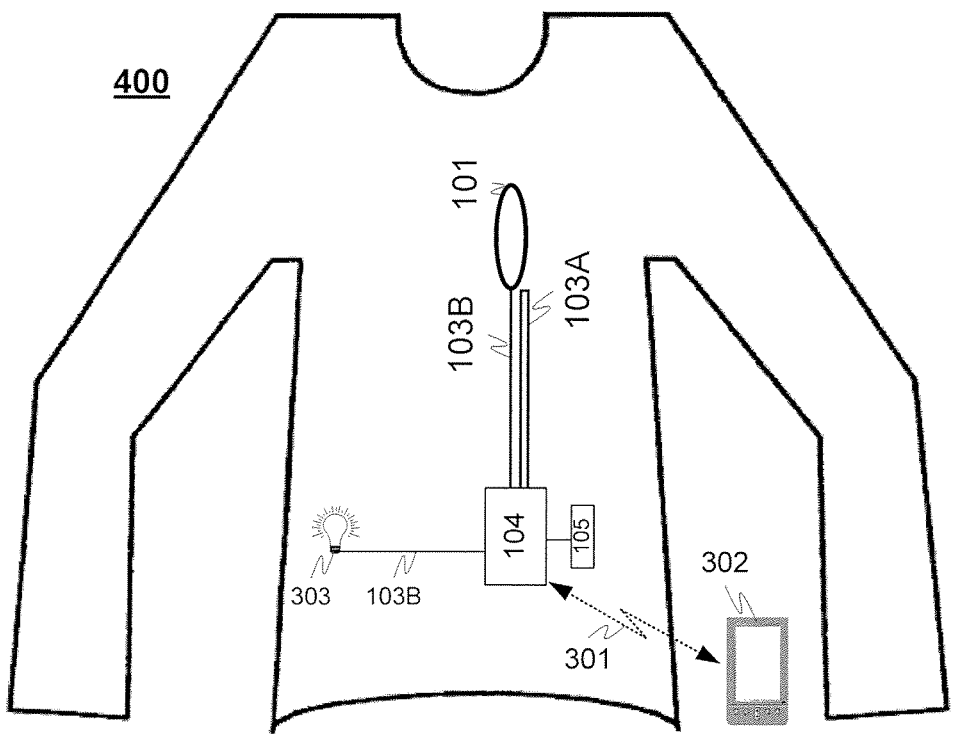
FIG. 10A illustrates exemplary wearable devices for determining effect or amount of aging according to an embodiment of the invention.
Figure 10B:
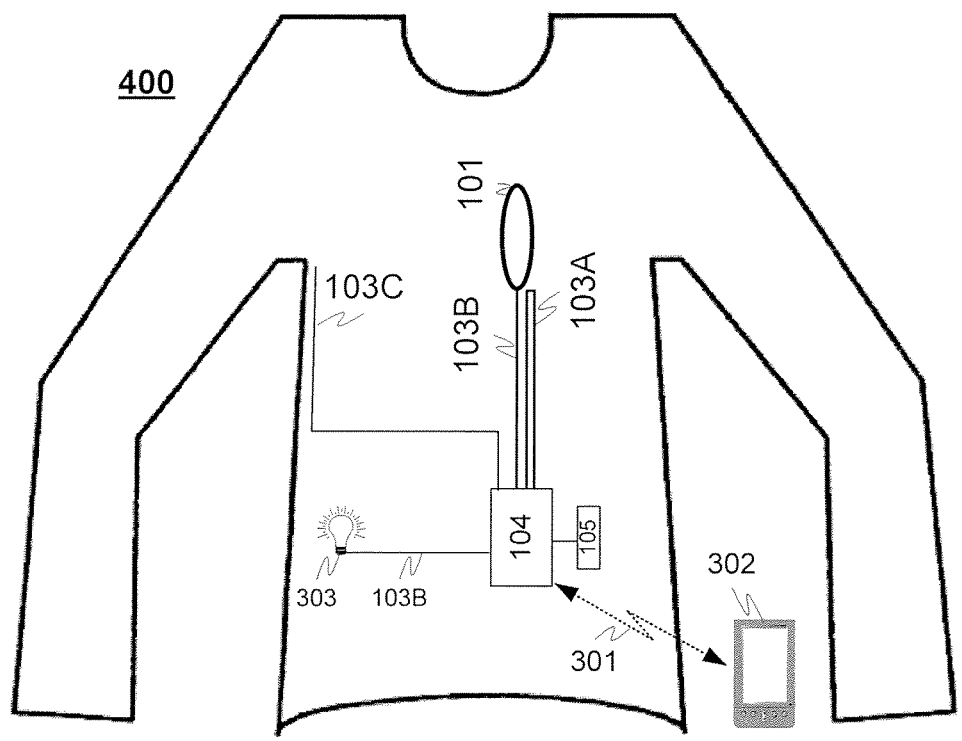
FIG. 10B illustrates exemplary wearable devices for determining effect or amount of aging according to an embodiment of the invention.

FIGS. 10A, 10B illustrate exemplary wearable devices 400 for determining effect or amount of aging according to an advantageous embodiment of the invention, where said wearable device comprises the arrangement 300 of FIG. 9 having at least one of the previous arrangements 200 illustrated in FIGS. 3-7 with the first and second transmitting loops.

In FIG. 10B the loops 103A, 103C are arranged in different locations of the wearable device so that another transmitting loop 103C will be exposed to higher erosion than the first transmitting loop 103A during usage, whereupon the aging can again be detected by comparing the different rates of changing of the properties, such as different rates of changing of resistances of the loops, as can be seen in diagram depicted in FIG. 8.

The invention has been explained above with reference to the aforementioned embodiments, and several advantages of the invention have been demonstrated. It is to be noted that even if the term loop is used, the measurements can also be done by one conductor. In addition it is clear that the invention is not only restricted to these embodiments, but comprises all possible embodiments within the spirit and scope of the inventive thought and the following patent claims. The features recited in dependent claims are mutually freely combinable unless otherwise explicitly stated.

In addition it is to be noted that the wearable device may comprise plurality of first transmitting loops and/or second transmitting loops with the same functional analogy as described in this document. Furthermore it is to be noted that at least one second transmitting loop may be used for powering the end device. Still on addition the arrangement may also control data transmission via the second transmitting loop, whereupon the manipulation may also comprise adapting line impedance of the data transmission loop or line based on the (changed) value of the property of the first transmitting loop. As an example the line impedance of the data transmission loop or line is typically 50Ω or 75Ω (Ohm). However, during the use of the wearable device the line impedance may change. Thus, according to the invention the data processing unit 104 may also perform active impedance matching to the transmission line (so the second transmitting loop used as said transmission line) so to keep the impedance of the line as desired. The impedance matching is advantageously done based on the (changed) value of the property of the first transmitting loop. Again it is to be noted that the first and second transmitting loops may be physically separate loops or the same transmitting loop.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:
1. A wearable device comprising:
a data processing unit;
a first transmitting loop coupled with the wearable device, the first transmitting loop having a measurable property which can be measured from the first transmitting loop; and
a second transmitting loop coupled with at least the wearable device, the second transmitting loop having a measurable property which can be measured from the second transmitting loop, wherein the first transmitting loop and the second transmitting loop are coupled at least one of galvanically and optically with the data processing unit, the measurable property with a readable value of the first transmitting loop and the measurable property with a readable value of the second transmitting loop vary in different ways in time and thereby the readable value of the first transmitting loop depends on amount of aging of the first transmitting loop and the readable value of the second transmitting loop depends on amount of aging of the second transmitting loop and thereby both values depend on aging of the wearable device to which the first transmitting loop and the second transmitting loop are coupled with, wherein the data processing unit is configured to measure a value of the measurable property of the first transmitting loop and a value of the measurable property of the second transmitting loop;

wherein the data processing unit is configured to determine amount of aging based on a different amount of change in measured values of the first transmitting loop and the second transmitting loop, wherein the difference of the measured values is compared to another predetermined measured difference value of the first transmitting loop and the second transmitting loop, and wherein the wearable device compensates the measured signals read via the second transmitting loop based on the determined amount of the aging.

2. The wearable device of claim 1, wherein the first transmitting loop and the second transmitting loop are separate transmitting loops.

3. The wearable device of claim 1, wherein:
the first measurable property and the second measurable property are at least one of an electrical and optical property.

4. The wearable device of claim 1, wherein the first transmitting loop and the second transmitting loop are separate transmitting loops and the first transmitting loop comprises a first material and the second transmitting loop comprises a second material, wherein the first material and the second material have different aging properties.

5. The wearable device of claim 1, wherein the first transmitting loop and the second transmitting loop are separate transmitting loops and the first transmitting loop comprises a first physical structure and the second transmitting loop comprises a second physical structure, wherein the first physical structure is configured to depend on aging differently than the second physical structure.

6. The wearable device of claim 1, wherein the first transmitting loop and the second transmitting loop are separate transmitting loops and the first transmitting loop is arranged in a first location of the wearable device and the second transmitting loop is arranged in a second location of the wearable device, wherein the first location and the second location are selected so that aging has a different effect on the first location as applicable to the first loop than on the second location as applicable to the second loop.

7. The wearable device of claim 1, wherein aging of the object comprises at least one of aging of the first transmitting loop, aging of the second transmitting loop, aging of the wearable device, and aging of a portion of the wearable device, and wherein the aging of the object causes changes to a measurable value of at least one of an electrical and optical property of at least one of the first transmitting loop and the second transmitting loop.

8. The wearable device of claim 1, wherein the wearable device is configured to manipulate power to the second transmitting loop which is coupled to and powers an end device.

9. The wearable device of claim 1, wherein the wearable device is configured to perform active impedance matching to the second transmitting loop functioning as a transmission line to keep an impedance of the transmission line as desired based on the value of the first measurable property of the first transmitting loop.

10. The wearable device of claim 1, wherein the wearable device is a garment or a structure portion of the garment selected from a group comprising: a strap, a belt, a heart rate sensor strap, a shirt, a sleeve, a portion of a shirt, leg, pocket, brand label, elastic portion of the garment, hat, bra, underwear, jacket, trousers, swimming suit, band, shoe, sock and glove.

11. The wearable device of claim 1, wherein the second transmitting loop is coupled to an end device and wherein the end device is a sensor for detecting at least one of biosignals, heart rate, respiration rate, posture of the user, temperature, humidity, conductivity, or acceleration.

12. The wearable device of claim 1, wherein an electrical property of the first transmitting loop and second transmitting loop is at least one of resistance, conductance, capacitance and inductance and an optical property is at least one of intensity, polarization or wavelength.

13. The wearable device of claim 1, wherein at least a portion of at least one of the first transmitting loop and the second transmitting loop is a printed conductive conductor.

14. The wearable device of claim 1, wherein the value of the first measurable property of the first transmitting loop is known at a first moment, and wherein the data processing unit is configured to measure a value of one of the first measurable property of the first transmitting loop and the second measurable property of the second transmitting loop when it is the same as the first transmitting loop at a second moment, the second moment being later than the first moment and to compare the measured values and determine effect of aging.

15. The wearable device of claim 1, wherein the wearable device is configured to provide notification of at least one of aging level of the object, notification that the object is over aged based on the determined effect or amount of aging, wherein the notification is provided to at least one of an indication device of the wearable device and an external device.

16. A wearable device comprising:
a data processing unit;
a first transmitting loop coupled with the wearable device, the first transmitting loop having a measurable property which can be measured from the first transmitting loop; and
a second transmitting loop coupled with at least the wearable device, the second transmitting loop having a measurable property which can be measured from the second transmitting loop,
wherein the first transmitting loop and the second transmitting loop are coupled with the data processing unit,
the measurable property with a readable value of the first transmitting loop and the measurable property with a readable value of the second transmitting loop vary in different ways in time and thereby the readable value of the first transmitting loop depends on amount of aging of the first transmitting loop and the readable value of the second transmitting loop depends on amount of aging of the second transmitting loop and thereby both values depend on aging of the wearable device to which the first transmitting loop and the second transmitting loop are coupled with, wherein the data processing unit is configured to measure a value of the measurable property of the first transmitting loop and a value of the measurable property of the second transmitting loop, wherein the data processing unit is configured to determine amount of aging based on a different amount of change in measured values of the first transmitting loop and the second transmitting loop, wherein the difference of the measured values is compared to another predetermined measured difference value of the first transmitting loop and the second transmitting loop, and wherein the wearable device compensates the measured signals read via the second transmitting loop based on the determined amount of the aging.

17. The wearable device of claim 16, wherein the first transmitting loop and the second transmitting loop are separate transmitting loops and the first measurable property and the second measurable property are a mutual property of at least two physically separate loops, wherein the mutual property is at least one of capacitance and resistance between the first transmitting loop and the second transmitting loop.

18. The wearable device of claim 16, wherein the first transmitting loop and the second transmitting loop are separate transmitting loops and the first transmitting loop comprises a first material and the second transmitting loop comprises a second material, wherein the first material and the second material have different aging properties.

19. The wearable device of claim 16, wherein the first transmitting loop and the second transmitting loop are separate transmitting loops and the first transmitting loop is arranged in a first location of the wearable device and the second transmitting loop is arranged in a second location of the wearable device, wherein the first location and the second location are selected so that aging has a different effect on the first location as applicable to the first loop than on the second location as applicable to the second loop.

* * * * *